United States Patent [19]

Turnbull et al.

[11] Patent Number: 5,358,670

[45] Date of Patent: Oct. 25, 1994

[54] PROCESS FOR PREPARING GRIGNARD REAGENTS IN DIETHYLENE GLYCOL DIBUTYL ETHER

[75] Inventors: Stanhope P. Turnbull, New Orleans; Charles R. Egedy, Baton Rouge, both of La.

[73] Assignee: Ferro Corporation, Cleveland, Ohio

[21] Appl. No.: 86,686

[22] Filed: Jul. 2, 1993

[51] Int. Cl.$^5$ ............................................. C07F 3/02
[52] U.S. Cl. ........................................... 260/665 G
[58] Field of Search ................................ 260/665 G

[56] References Cited

U.S. PATENT DOCUMENTS

| | | | |
|---|---|---|---|
| 2,552,676 | 5/1951 | Hill | 260/665 |
| 2,838,508 | 6/1958 | Ramsden | 260/247 |
| 3,758,620 | 9/1973 | Vit | 260/665 |

OTHER PUBLICATIONS

A Novel, Continuous High-Yield Synthesis Of Grignard Reagents J. R. Jennings, Journal of Organometallic Chemistry 1987 vol. 325 pp. 25–29.

An Improved Preparation of a Grignard Reagent, T. S. Eckert, Journal of Chemical Education, 1987 vol. 64 p. 179.

Preparation Of Grignard Reagents By Continuous Process, Thust et al, Chemical Abstracts, vol. 110 1989, p. 740.

Method For The Preparation Of di-Grignard Reagent Phenylenebis (magnesium chloride), Wang et al., Chemical Abstracts, vol. 114, 1991 p. 837.

Preparation Of Pyridyl Grignard Reagents And Cross Coupling Reactions With Sulfoxides Bearing Aza-eheterocycles, Furukawa et al, Tetrahedron Letters, vol. 28 1987 pp. 5845–5848.

Mechanical Activation Of Magnesium Turnings For The Preparation Of Reactive Grignard Reagents, Baker et al., J. Org. Chem. 1991, 56, pp. 698–703.

Preparation of Grignard-type Organometallic Compounds, Z. Wirpsza, Chemical Abstracts, vol. 110, 1989, p. 13.

*Primary Examiner*—Jose' G. Dees
*Assistant Examiner*—Porfirio Nazario-Gonzalez
*Attorney, Agent, or Firm*—Rankin, Hudak & Hill

[57] ABSTRACT

This invention relates to an alkyl Grignard reagents in diethylene glycol dibutyl ether. The invention also relates to a novel method for preparing Grignard reagents comprising reacting an alkyl halide with magnesium metal in the presence of diethylene glycol dibutyl ether. Grignard reagents prepared in the presence of diethylene glycol dibutyl ether have improved yields and stability, including storage stability, at room temperature. The Grignard reagents are prepared without the use of a low boiling and/or flammable stabilizing agents such as benzene, toluene, tetrahydrofuran, and diethyl ether.

3 Claims, No Drawings

PROCESS FOR PREPARING GRIGNARD REAGENTS IN DIETHYLENE GLYCOL DIBUTYL ETHER

FIELD OF THE INVENTION

This invention relates to a process for preparing Grignard reagents in the diethylene glycol butyl ether and methods of making the same.

BACKGROUND OF THE INVENTION

Grignard reagents are prepared by the reaction of magnesium metal with an organic halide. Grignard reagents have been prepared in the presence of ether solvents and tetrahydrofuran. It is known that the preparation of Grignard reagents are often quite difficult. Formation of these reagents is inhibited by the presence of water and alcohols, ethers and halides and by impurities on the surface of the magnesium turnings.

U.S. Pat. No. 2,552,676 relates to a method of manufacturing organometallic compounds. This process involves reacting organic halides with magnesium in the presence of glycol ethers. Alkyl Grignard reagents are described prepared from ethylene glycol diethyl ether, diethylene glycol diethyl ether, and tetraethylene glycol dimethyl ether. Aryl Grignard reagents are described which are prepared from ethylene glycol diethyl ether, ethylene glycol dimethyl ether, ethylene glycol n-butyl ethyl ether, diethylene glycol n-butyl ethyl ether, diethylene glycol diethyl ether, ethylene glycol, dibutyl ether, and tetraethylene glycol dimethyl ether.

U.S. Pat. No. 2,838,508 relates to a chemical process involving separating Grignard reagents from saturated or ethylenically unsaturated cyclic ethers. The process involves mixing a Grignard reagent, which is in the presence of tetrahydrofuran, with ethylene glycol or polyethylene glycol. The ethylene glycol or polyethylene glycol separates the tetrahydrofuran from the Grignard reagent and allows removal of tetrahydrofuran.

U.S. Pat. No. 3,758,620 relates to a process for preparing Grignard reagents. The process involves treating solvent systems such as ether solvents, diethyl ether, tetrahydrofuran, dibutyl ether and 1,2 dimethoxyethane with reducing halides. The addition of the hydride reduces and or eliminates the induction period which occur in most preparations of Grignard reagents.

It is desirable to have a solvent which may be used in the preparation of the Grignard reagent and not form precipitate upon cooling of the Grignard reaction. Further, it is desirable to have high boiling solvents used in the preparation of Grignard reagents.

SUMMARY OF THE INVENTION

This invention relates to an alkyl Grignard reagents in diethylene glycol dibutyl ether. The invention also relates to a novel method for preparing Grignard reagents comprising reacting an alkyl halide with magnesium metal in the presence of diethylene glycol dibutyl ether.

Grignard reagents prepared in the presence of diethylene glycol dibutyl ether have improved yields and stability, including storage stability, at room temperature. The Grignard reagents are prepared without the use of a low boiling and/or flammable stabilizing agents such as benzene, toluene, tetrahydrofuran, and diethyl ether.

DESCRIPTION OF THE PREFERRED EMBODIMENTS

The present invention relates to alkyl Grignard reagents in diethylene glycol dibutyl ether. In one embodiment the mixture is free of stabilizing agents such as diethyl ether, tetrahydrofuran, benzene, and toluene. It has been discovered that alkyl Grignard reagent and diethylene glycol dibutyl ether mixtures are stable and do not require the presence of these stabilizing agents.

The present invention also relates to an application of preparing Grignard reagents from organic halides and magnesium metal. The reaction occurs in the presence of diethylene glycol dibutyl ether. The organic halides include alkyl or aryl halides. Examples of useful halides include chlorides and bromides, preferably chlorides. Examples of alkyl halides include methyl chloride, butyl chloride, and propyl chloride. The examples of aryl halides include phenylchloride.

The first step of the process involves reacting an organic halide with magnesium metal. This reaction produces heat and the temperature of the reaction increases. Generally, the reaction temperature increases to about 70° C. The reaction temperature is generally maintained from about 50° C., up to about 100° C., or preferably from about 60° C., up to about 80° C. The reaction generally takes from about 0.5, to about 10 hours, or preferably from about 1 hour up to about 5 hours. Here, as well as elsewhere in the specification, the ratio and range limits may be combined. Typically, the reaction time is about 4–5 hours. After disappearance of the magnesium metal, the reaction mixture is cooled to room temperature. In one embodiment, the reaction occurs in the absence of stabilizing agents. Previously, stabilizing agents were required to enhance Grignard formation and prevent precipitation of the Grignard reagents. Examples of stabilizers include diethyl ether, tetrahydrofuran, benzene, and toluene.

The following examples relate to preparation of Grignard reagents with diethylene glycol dibutyl ether. Throughout the specification and claims, unless the context indicates otherwise, temperature is in degrees celsius, pressure is atmospheric pressure, and parts and percentages are by weight.

EXAMPLE 1

A dry, stirred 12-liter flask is charged with 366.6 grams of magnesium turnings and 5 liters of diethylene glycol dibutyl ether. The ether solvent is previously purified by distillation and stored over sieves. The mixture is heated to 45 degrees centigrade and dry methyl chloride gas is sparged into the solution. Methyl chloride is recovered and returned to the pot by use of a cold finger apparatus chilled with a carbon dioxide-acetone slush. The reaction starts after ten minutes. The temperature is maintained at 65–70 degrees centigrade during methyl chloride addition. After 4 hours most of the magnesium has reacted. The mixture is then sparged with dry nitrogen for 2 hours, to remove excess methyl chloride, during which time the remaining magnesium metal reacts. The Grignard reagent is then stored under nitrogen.

EXAMPLE 2

A solution of 68.5 grams of ethyl bromide in 50 milliliters of diethylene glycol dibutyl ether is added dropwise over 0.5 hours to a mixture of 200 milliliters of the ether solvent and 15.41 grams of magnesium turnings at 40 degrees. The reaction starts after 10 minutes and proceeds for 1 hour.

EXAMPLE 3

The same procedure in Example 2 is used to prepare methyl magnesium iodide in diethylene glycol dibutyl ether. The reaction is complete in 3 hours.

As can be seen from the above examples, Grignard reagents may be prepared with diethylene glycol dibutyl ether. These Grignard reagents do not require the presence of stabilizing agents, such as diethyl ether, tetrahydrofuran, benzene and toluene.

The following comparative examples relate to Grignard reagents prepared with other ethylene glycol or diethylene glycol dialkyl ethers.

EXAMPLE A

A mixture of 3 grams of magnesium turnings and 235 mls of previously distilled diethylene glycol dimethyl ether is sparged with methyl chloride gas at 50 degrees for 3 hours. No reaction occurs.

EXAMPLE B

Methyl chloride is sparged into a mixture of 33.5 grams of magnesium turnings and 500 mls of diethylene glycol diethyl ether. The mixture temperature is maintained at 80-85 degrees for 2 hours until all of the magnesium has reacted. The reaction is then cooled unaided. A crystalline precipitate fills the volume of the mixture at 45 degrees. Tetrahydrofuran is added dropwise to make a 17% solution. The solid dissolves and the solution remains homogeneous.

EXAMPLE C

A solution of 66.3 grams of ethyl bromide and 100 mls of diethylene glycol diethyl ether are added dropwise to a mixture of 16.3 grams of magnesium turnings and 150 mls of diethylene glycol diethyl ether at 40 degrees. The reaction is complete in 5 hours. Tetrahydrofuran is added to make a 30% solution which remains homogeneous.

EXAMPLE D

A mixture of 18.4 grams of magnesium turnings and 250 mls of previously distilled ethylene glycol dibutyl ether is sparged with methyl chloride at 40-50 degrees. After 1.5 hours of sparging a fine white solid precipitates. Addition of tetrahydrofuran does not dissolve the precipitate and a homogeneous solution is not formed.

As can be seen from the above examples, tetrahydrofuran has been added to Examples A-C to make homogeneous solutions. Example D does not produce a homogeneous solution even with the use of tetrahydrofuran. As has been described above, the inventors have discovered a novel process of preparing homogeneous Grignard reagents without the use of tetrahydrofuran or other stabilizers.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A novel method for preparing Grignard reagents comprising the steps of: (1) reacting an organic halide with magnesium metal in the presence of diethylene glycol dibutyl ether, and (2) cooling the mixture to room temperature, wherein the process occurs in the absence of tetrahydrofuran, benzene, toluene, and diethyl ether stabilizing agents.

2. The process of claim 1, wherein said organic halide is an alkyl halide.

3. The process of claim 1, wherein said organic halide is an alkyl chloride.

* * * * *